(12) United States Patent
Miyakawa et al.

(10) Patent No.: US 11,618,770 B2
(45) Date of Patent: Apr. 4, 2023

(54) MUC1-DERIVED PEPTIDE, AND PHARMACEUTICAL COMPOSITION FOR TREATMENT OR PREVENTION OF CANCER, IMMUNITY-INDUCING AGENT AND METHOD FOR MANUFACTURING ANTIGEN PRESENTING CELL USING SAME

(71) Applicant: NEC CORPORATION, Tokyo (JP)

(72) Inventors: Tomoya Miyakawa, Tokyo (JP); Masaaki Oka, Yamaguchi (JP); Shoichi Hazama, Ube (JP); Koji Tamada, Ube (JP); Keiko Udaka, Nankoku (JP)

(73) Assignee: NEC CORPORATION, Tokyo (JP)

( * ) Notice: Subject to any disclaimer, the term of this patent is extended or adjusted under 35 U.S.C. 154(b) by 194 days.

(21) Appl. No.: 16/795,391

(22) Filed: Feb. 19, 2020

(65) Prior Publication Data

US 2020/0181195 A1 Jun. 11, 2020

Related U.S. Application Data

(63) Continuation of application No. 15/556,766, filed as application No. PCT/JP2016/057349 on Mar. 9, 2016, now abandoned.

(30) Foreign Application Priority Data

Mar. 9, 2015 (JP) ................. 2015-046462

(51) Int. Cl.
| | |
|---|---|
| *A61K 39/00* | (2006.01) |
| *C07K 7/06* | (2006.01) |
| *C12N 5/10* | (2006.01) |
| *A61K 38/00* | (2006.01) |
| *C07K 14/47* | (2006.01) |
| *C07K 14/705* | (2006.01) |

(52) U.S. Cl.
CPC ............. *C07K 7/06* (2013.01); *A61K 38/00* (2013.01); *A61K 39/00* (2013.01); *C07K 14/47* (2013.01); *C07K 14/705* (2013.01); *C12N 5/10* (2013.01)

(58) Field of Classification Search
CPC ........ C07K 7/06; C07K 14/47; C07K 14/705; A61K 38/00; A61K 39/00; C12N 5/10
See application file for complete search history.

(56) References Cited

U.S. PATENT DOCUMENTS

| | | | | |
|---|---|---|---|---|
| 2005/0142640 | A1* | 6/2005 | Taylor-Papadimitriou | ................. A61P 37/06 435/69.1 |
| 2009/0023895 | A1 | 1/2009 | Miyakawa et al. | |
| 2011/0318380 | A1* | 12/2011 | Brix | ........ A61P 37/04 424/193.1 |
| 2015/0322112 | A1* | 11/2015 | Tsunoda | ........ C07K 16/28 424/185.1 |

FOREIGN PATENT DOCUMENTS

| | | |
|---|---|---|
| CN | 104211796 A | 12/2014 |
| JP | 08-151396 A | 6/1996 |
| JP | 11-316754 A | 11/1999 |
| JP | 2003-510094 A | 3/2003 |
| WO | 01/18035 A2 | 3/2001 |
| WO | 01/18035 A3 | 3/2001 |
| WO | 2006/004182 A1 | 1/2006 |
| WO | 2007/091387 A1 | 8/2007 |
| WO | 2010/037395 A2 | 4/2010 |

OTHER PUBLICATIONS

Harig et al (Blood, 98: 2999-3005, 2001 (Year: 2001).*
Peter L. Devine et al., "Mucins: Structure, function, and associations with malignancy", BioEssays, Sep. 1992, pp. 619-625, vol. 14, Issue 9.
Sandra J. Gendler et al., "Molecular Cloning and Expression of Human Tumor-associated Polymorphic Epithelial Mucin", The Journal of Biological Chemistry, Sep. 1990, pp. 15286-15293, vol. 265, No. 25.
Franz-Georg Hanisch et al., "MUC1 glycoforms in breast cancer—Cell line T47D as a model for carcinoma-associated alterations of O-glycosylation", Eur. J. Biochem., 1996, pp. 318-327, vol. 236.
Donna L. Barnd et al., "Specific, major histocompatibility complex-unrestricted recognition of tumor-associated mucins by human cytotoxic T cells", Proc. Natl. Acad. Sci. USA, pp. 7159-7163, Sep. 1989, vol. 86.
Keith R. Jerome et al., "Cytotoxic T-Lymphocytes Derived from Patients with Breast Adenocarcinoma Recognize an Epitope Present on the Protein Core of a Mucin Molecule Preferentially Expressed by Malignant Cells", Cancer Research, Jun. 1, 1991, pp. 2908-2916, vol. 51.
Constantin G. Ioannides et al., "Cytotoxic T Cells Isolated from Ovarian Malignant Ascites Recognize a Peptide Derived from the HER-2/neu Proto-oncogene", Cellular Immunology, 1993, pp. 225-234, vol. 151, Issue 1.
Ralph T. Kubo et al., "Definition of specific peptide motifs for four major HLA-A Alleles", The Journal of Immunology, 1994, pp. 3913-3924, vol. 152, Issue 8.
Hans-Georg Rammensee et al., "MHC ligands and peptide motifs: first listing", Immunogenetics, 1995, pp. 178-228, vol. 41.
Akihiro Kondo et al., "Prominent Roles of Secondary Anchor Residues in Peptide Binding to HLA-A24 Human Class I Molecules", The Journal of Immunology, 1995, pp. 4307-4312, vol. 155, Issue 9.
Keiko Udaka et al., An automated prediction of MHC class I-binding peptides based on positional.
International Search Report of PCT/JP2016/057349 dated Jun. 7, 2016.

\* cited by examiner

*Primary Examiner* — Lei Yao
(74) *Attorney, Agent, or Firm* — Sughrue Mion, PLLC

(57) ABSTRACT

The present invention provides a peptide that includes eight or more consecutive amino acid residues of amino acid sequence of one of Sequence ID Nos. 1 to 12 and that consists of eleven or less amino acid residues.

4 Claims, 2 Drawing Sheets
Specification includes a Sequence Listing.

US 11,618,770 B2

MUC1-DERIVED PEPTIDE, AND PHARMACEUTICAL COMPOSITION FOR TREATMENT OR PREVENTION OF CANCER, IMMUNITY-INDUCING AGENT AND METHOD FOR MANUFACTURING ANTIGEN PRESENTING CELL USING SAME

CROSS-REFERENCE TO RELATED APPLICATIONS

This application is a Continuation of U.S. application Ser. No. 15/556,766 filed Sep. 8, 2017, which is a National Stage of International Application No. PCT/JP2016/057349 filed Mar. 9, 2016, claiming priority based on Japanese Patent Application No. 2015-046462 filed Mar. 9, 2015, the contents of all of which are incorporated herein by reference in their entirety.

TECHNICAL FIELD

The present invention relates to an MUC1-derived peptide, more specifically an immunogenic peptide that binds to a human leukocyte antigen and thus presents an antigen to a T cell, and a pharmaceutical composition for treatment or prevention of cancer, an immunity-inducing agent, a method for manufacturing an antigen presenting cell and the like, using the same.

BACKGROUND ART

It is thought that cancer cells always occur accidentally in living bodies. It is likely that a reaction in which specific cancer antigens derived from cancer cells are eliminated by natural immunity usually occurs, and then a specific immune response is induced, so that a reaction in which the cancer cells are eliminated by lymphocytes and the like occurs.

The formation of a complex between a human leukocyte antigen (HLA) that is present on the cell surface and a lymphocyte is necessary for recognition of antigens derived from cancer cells. HLA molecules, which are major histocompatible antigens, are broadly divided into class-I molecules (HLA-A, -B, and -C) and class-II molecules (HLA-DP, -DQ, and -DR). T cell antigen receptors (TCRs) on cytotoxic T cells (CTLs) specifically recognize cancer antigens (CTL epitopes) consisting of 8 to 11 amino acids presented to HLA class-I molecules on the surfaces of cancer cells, and thus a reaction in which cancer cells are eliminated by the CTLs is induced.

Nowadays, a search for immunogenic peptides is made with the expectation of the application to treatment or prevention of various immunological diseases. For example, JP H8-151396A discloses that oligopeptides having specific amino acid sequences have an HLA-binding property.

CITATION LIST

Patent Document

Patent Document 1: JP H8-151396A

SUMMARY OF THE INVENTION

Technical Problem

Although a large number of peptides having an HLA-binding property are known, further peptides that can be used for treatment or prevention of various cancers are required. The gene for HLA is rich in polymorphism, and therefore, multi-type immunogenic peptides that can be applied to a plurality of types of HLAs are also required.

Solution to Problem

The present invention has been achieved in light of the aforementioned circumstances, and an object thereof is to provide an immunogenic peptide that binds to an HLA class-I molecule, particularly a peptide that can induce CTLs, and a pharmaceutical composition for treatment or prevention of cancer, an immunity-inducing agent, a method for manufacturing an antigen presenting cell and the like, using the same.

That is, the present invention encompasses the following aspects of the invention.

(1) A peptide including eight or more consecutive amino acid residues of amino acid sequence of one of Sequence ID Nos. 1 to 12, and consisting of eleven or less amino acid residues.

(2) The peptide according to aspect (1), wherein one or several amino acids in the amino acid sequence are substituted, inserted, deleted, or added, and the peptide has immunogenicity.

(3) The peptide according to aspect (2), wherein an amino acid at a 2-position of the amino acid sequence is substituted with tyrosine, phenylalanine, methionine, tryptophan, valine, leucine or glutamine, and/or a C-terminal amino acid is substituted with phenylalanine, leucine, isoleucine, tryptophan, methionine, or valine.

(4) A pharmaceutical composition for treatment or prevention of cancer, comprising the peptide according to any one of aspects (1) to (3).

(5) The pharmaceutical composition according to aspect (4), which is in a form of vaccine.

(6) The pharmaceutical composition according to aspect (4) or (5), wherein the peptide can bind to one or more types of HLA molecules.

(7) An immunity-inducing agent comprising the peptide according to any one of aspects (1) to (3).

(8) The immunity-inducing agent according to aspect (7), which is used to induce a cytotoxic T cell.

(9) The immunity-inducing agent according to aspect (7) or (8), wherein the peptide can bind to one or more types of HLA molecules.

(10) A method for manufacturing an antigen presenting cell having a CTL-inducing activity, the method comprising a step of bringing the peptide according to any one of aspects (1) to (3) into contact with an antigen presenting cell in vitro.

Advantageous Effects of Invention

In recent years, an immunotherapy has been attracting attention as treatment of cancer. The peptide of the present invention has a high HLA-binding property and a high ability to induce CTLs, and is thus strongly expected to be useful as a cancer vaccine. Moreover, it is likely that the peptide of the present invention can be applied to various immunotherapies, particularly to a dendritic cell therapy.

Mucin is a large glycoprotein that is expressed in various epithelial cells including normal cells and malignant cells (Devine PL and McKenzie IF: Mucins: structure, function, and associations with malignancy. Bioessays 14: 619-625, 1992). MUC1, which is one of mucin polypeptides, is a unique glycoprotein that is expressed passing through the cell membrane on a cell surface (Gendler S J, Lancaster C A, Taylor-Papadimitriou J, Duhig T, Peat N, Burchell J, Pemberton L, Lalani E N and Wilson D: Molecular cloning and expression of human tumor-associated polymorphic epithelial mucin. J Biol Chem 265: 15286-15293, 1990).

MUC1 of cancer cells undergoes incomplete glycosylation (Hanisch F G, Stadie T R, Deutzmann F and Peter-Katalinic J: MUC1 glycoforms in breast cancer—cell line T47D as a model for carcinoma-associated alterations of O-glycosylation. Eur J Biochem 236: 318-327, 1996.), and it has been reported that killer T cells against MUC1 are induced in pancreatic cancer, breast cancer, ovarian cancer, and the like (20 Barnd D L, Lan M S, Metzgar R S and Finn O J: Specific, major histocompatibility complex-unrestricted recognition of tumorassociated mucins by human cytotoxic T cells. Proc Natl Acad Sci USA 86: 7159-7163, 1989.

21 Jerome K R, Barnd D L, Bendt K M, Boyer C M, Taylor-Papadimitriou J, McKenzie I F, Bast R C Jr and Finn O J: Cytotoxic T-lymphocytes derived from patients with breast adenocarcinoma recognize an epitope present on the protein core of a mucin molecule preferentially expressed by malignant cells. Cancer Res 51: 2908-2916, 1991.

22 Ioarmides C G, Fisk B, Fan D, Biddison W E, Wharton J T and O'Brian C A: Cytotoxic T cells isolated from ovarian malignant ascites recognize a peptide derived from the HER-2/neu protooncogene. Cell Immunol 151: 225-234, 1993.).

Specific aspects of the peptide of the present invention can bind to a plurality of types of HLAs. Therefore, with the peptide of the present invention, a cancer vaccine, a dendritic cell therapy, and the like that cover an extremely broad group of cancer patients can be provided.

DESCRIPTION OF EMBODIMENTS

1. Immunogenic Peptide

Figure 1:
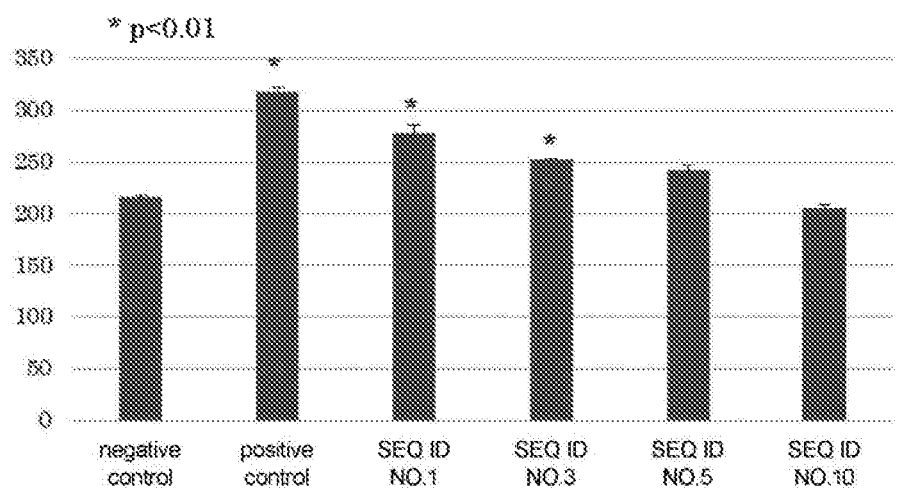
FIG. 1 shows results (the number of IFN-γ producing cells) of ELISA assay when samples from a patient (HLA type: 24:02/33:03) that has undergone a dendritic cell/CTL therapy against MUC1 are stimulated using peptides of Sequence ID Nos. 1, 3, 5, and 10.

A peptide according to the present invention is a peptide that includes eight or more consecutive amino acid residues of the amino acid sequence of one of Sequence ID Nos. 1 to 12, and that consists of eleven or less amino acids, preferably ten or less amino acids, and more preferably nine or less amino acids, in total. The peptide of the present invention may also have the amino acid sequence of one of Sequence ID Nos. 1 to 12. The peptide of the present invention is derived from mucin 1 (MUC1), which is one of tumor-associated antigens.

Selected were the amino acid sequences that were based on the amino acid sequence of MUC1 and whose HLA molecule-binding properties predicted based on the hypothesis obtained by using an active learning experiment method (JP H11-316754A) were 3 or more in terms of a-logKd value.

Table 1 below shows the amino acid sequences for the peptide of the present invention, and the predicted HLA-binding scores.

TABLE 1

| Amino acid sequence | Location in | Predicted binding score | | |
|---|---|---|---|---|
| (Sequence ID No.) | MUC1 | to A*24:02 | to A*02:01 | to A*02:06 |
| FLGLSNIKF (Seq. ID No. 1) | 1086 | 5.0955 | 4.4235 | 4.1939 |
| SVPVTRPAL (Seq. ID No. 2) | 100 | 5.0767 | 4.4656 | 5.8224 |
| GVPGWGIAL (Seq. ID No. 3) | 1155 | 4.9066 | 4.5398 | 5.3254 |
| AFREGTINV (Seq. ID No. 4) | 1106 | 4.6737 | 4.6098 | 4.4007 |
| AASRYNLTI (Seq. ID No. 5) | 1128 | 4.5613 | 4.2522 | 4.1161 |
| LQRDISEMF (Seq. ID No. 6) | 1069 | 5.4895 | 3.9363 | 3.812 |
| HHSDTPTTL (Seq. ID No. 7) | 997 | 5.2785 | 3.8534 | 4.0609 |
| SFFFLSFHI (Seq. ID No. 8) | 1041 | 5.0343 | 4.5581 | 3.958 |
| TLAFREGTI (Seq. ID No. 9) | 1104 | 4.8467 | 4.8911 | 3.9425 |
| STGVSFFFL (Seq. ID No. 10) | 1037 | 4.7519 | 4.0289 | 5.2728 |
| GQDVTSVPV (Seq. ID No. 11) | 95 | 3.7866 | 5.1026 | 6.1919 |
| FSAQSGAGV (Seq. ID No. 12) | 1148 | 3.0319 | 5.2427 | 4.0462 |

The peptide of the present invention has an HLA-binding property and immunogenicity (also referred to merely as "HLA peptide" or "immunogenic peptide" hereinafter). "Immunogenicity" as used herein means an ability to induce an immune reaction, and, for example, means "having a CTL-inducing activity and thus a cytotoxic activity against cancer cells".

In a preferred aspect, the peptide of the present invention is a multi-HLA peptide that can bind to a plurality of types of alleles of the HLA-A gene A. For example, the peptide of Sequence ID No. 10 strongly binds to an HLA-A*24:02 gene product (HLA-A*24:02 molecule), an HLA-A*02:01 gene product (HLA-A*02:01 molecule), and an HLA-A*02:06 gene product (HLA-A*02:06 molecule), and has a high immunogenicity.

HLA subtypes to which the peptide of the present invention can bind are not limited to the HLA-A*24:02, the HLA-A*02:01, and the HLA-A*02:06. However, about 85% of the Oriental including Japanese and about 55% of the Occidental have these HLA subtypes, and therefore, it is thought that the multi-HLA peptide has a high patient cover ratio in an immunotherapy or the like.

Amino acid residues of the amino acid sequences of Sequence ID Nos. 1 to 12 or portions thereof may be modified as long as the peptide of the present invention retains immunogenicity. The amino acid sequences of Sequence ID Nos. 1 to 12 are intended to be presented on antigen presenting cells, but, when being administered directly to the body, the peptide of the present invention may undergo a modification such as digestion of its terminus in the digestive organs depending on the administration route. Therefore, prior to being taken up by an antigen presenting cell, the peptide of the present invention may exist in a precursor form in which one or more amino acid residues and the like are added to the N-terminus and/or C-terminus such that the peptide of the present invention retains the amino acid residues of Sequence ID Nos. 1 to 12 when binding to a predetermined HLA class-I molecule on the antigen presenting cell.

Furthermore, in the peptide of the present invention, one or several amino acid residues of the peptide of the present invention may be substituted, inserted, deleted, or added, and/or the peptide of the present invention may undergo modifications such as glycosylation, side-chain oxidation and/or phosphorylation. The "amino acids" are used herein in their broadest sense, and include artificial amino acid variants and artificial amino acid derivatives in addition to natural amino acids. In this specification, examples of the amino acids include natural protein L-amino acids; D-amino acids; chemically modified amino acids such as amino acid variants and amino acid derivatives; non-protein natural amino acids such as norleucine, β-alanine, and ornithine; and chemically synthesized compounds having characteristics known in the art as features of amino acids. Examples of non-natural amino acids include a-methylamino acids (e.g., α-methylalanine), D-amino acids, histidine-like amino acids (e.g., β-hydroxy-histidine, homohistidine, α-fluoromethyl-histidine, and α-methyl-histidine), amino acids with side chains including additional methylenes (i.e., "homo-"amino acids), and substituted amino acids (e.g., cysteic acid) in which a carboxylic acid functional group in a side chain is substituted with a sulfonic acid.

Regarding the substitution of amino acid residues and the like, a person skilled in the art could substitute the amino acids of the peptide of the present invention as appropriate in consideration of the regularity of peptide sequences exhibiting an HLA-binding property (J. Immunol., 152: p 3913, 1994; Immunogenetics, 41: p 178, 1995; J. Immunol., 155: p 4307, 1995).

More specifically, in the case of a peptide that binds to the HLA-A*24:02 molecule, the amino acid at the 2-position of the peptide may be substituted with tyrosine, phenylalanine, methionine, or tryptophan, and/or the C-terminal amino acid may be substituted with phenylalanine, leucine, isoleucine, tryptophan, or methionine. In the case of a peptide that binds to the HLA-A*02:01 molecule, the amino acid at the 2-position may be substituted with leucine or methionine, and/or the C-terminal amino acid may be substituted with valine or leucine. Furthermore, in the case of a peptide that binds to the HLA-A*02:06 molecule, the amino acid at the 2-position may be substituted with valine or glutamine, and/or the C-terminal amino acid may be substituted with valine or leucine.

All aspects of the peptide of the present invention can be manufactured using methods known to a person skilled in the art. For example, the peptide of the present invention may be synthesized artificially using a solid phase method such as the Fmoc method or the tBoc method, or a liquid phase method. Moreover, a desired peptide may also be manufactured by expressing a polynucleotide coding for the peptide of the present invention or a recombinant vector including the polynucleotide. All of the thus obtained peptides can be identified using a method known to a person skilled in the art. For example, the peptides can be identified using the Edman degradation method, mass spectrometry, or the like.

2. Pharmaceutical Composition

A pharmaceutical composition for treatment or prevention of cancer according to the present invention contains, as an active component, a peptide that includes eight or more consecutive amino acid residues of one or more amino acid sequences selected from the group consisting of Sequence ID Nos. 1 to 12, and that consists of eleven or less amino acids, preferably ten or less amino acids, and more preferably nine or less amino acids, in total, for example. The peptide contained in the pharmaceutical composition may also have the amino acid sequence of one of Sequence ID Nos. 1 to 12. The peptide is as defined above.

The peptide of the present invention is presented on an antigen presenting cell and thus induces CTLs, and the induced CTLs injure cancer cells. Therefore, the active component of the pharmaceutical composition of the present invention is not limited to the peptide of the present invention, and may be a component that can induce CTLs directly or indirectly. For example, a polynucleotide coding for the peptide or a vector including the polynucleotide, an antigen presenting cell that presents a complex between the peptide and an HLA molecule on its surface, or an exosome secreted by the antigen presenting cell, or combinations thereof may be used. Examples of the antigen presenting cell to be used include a macrophage and a dendritic cell, and it is preferable to use a dendritic cell, which has a high ability to induce CTLs. The pharmaceutical composition of the present invention may also contain other components known to be used for treatment of cancer, such as a chemokine, a cytokine, a tumor necrosis factor, and a chemotherapeutic agent. A peptide dosage may be about 1 to 10 mg per day, for example, when a patient is an adult. However, the dosage varies depending on the age and weight of a patient, an administration method, and the like, and therefore, a person skilled in the art determines the dosage as appropriate.

The pharmaceutical composition of the present invention is not construed as being limited, but is thought to be useful for killing or the like of cancer cells due to the following action mechanism. When the pharmaceutical composition of the present invention is administered to a specific cancer patient, the peptide in the pharmaceutical composition is presented on the surface of the antigen presenting cell in a state in which the peptide binds to an HLA molecule. The CTLs recognize the peptide on such an antigen presenting cell and is thus activated, followed by proliferation and systemic circulation. When CTLs that are specific to the peptide enter the cancer tissue, the CTLs recognize the same peptide derived from the specific cancer antigen that naturally binds to the HLA molecule present on the surface of the cancer cell, and then kill the cancer cell. The pharmaceutical composition can contribute to treatment of cancer due to this action.

The pharmaceutical composition can be used for not only treatment of cancer but also prevention of cancer. For example, when the pharmaceutical composition of the present invention is administered to a healthy human body, CTLs are induced, and the induced CTLs remain in the body. Therefore, when a specific cancer occurs, it is possible to injure the cancer cells. Similarly, a recurrence of cancer may be prevented by the administration to the human body that has undergone treatment of cancer.

All cancers in which MUC1 is expressed are assumed as cancer to be treated or prevented. More specifically, examples of target cancers include pancreatic cancer, hepatocellular cancer, prostate cancer, lung cancer, breast cancer, bowel cancer, blood cancer, brain tumor, kidney cancer, and skin cancer, but are not construed as being limited. For example, MUC1 from which the peptide of the present invention is derived is overexpressed in pancreatic cancer, and therefore, it is thought that the peptide of the present invention is effective in treatment or prevention of pancreatic cancer. When a plurality of types of cancers to be treated or prevented are present, the pharmaceutical composition of the present invention can contain a plurality of types of active components such as an immunogenic peptide.

The pharmaceutical composition of the present invention can be administered to a patient in a form of a preparation of a pharmaceutically acceptable salt obtained by dissolving the pharmaceutical composition in a water-soluble solvent. Examples of the form of such a pharmaceutically acceptable salt include forms of a physiologically acceptable water-soluble salt such as a sodium salt, a potassium salt, a magnesium salt, or a calcium salt that is buffered at a physiological pH. A water-insoluble solvent can also be used in addition to a water-soluble solvent, and examples of the water-insoluble solvent include alcohols such as ethanol and propylene glycol.

A preparation containing the pharmaceutical composition of this embodiment can contain agents for various purposes, and examples of such agents include a preservative and a buffer. Examples of the preservative include sodium bisulfate, sodium bisulfate, sodium thiosulfate benzalkonium chloride, chlorobutanol, thimerosal, phenylmercuric acetate, phenylmercuric nitrate, methylparaben, polyvinyl alcohol, phenylethyl alcohol, ammonia, dithiothreitol, and β-mercaptoethanol. Examples of the buffer include sodium carbonate, sodium borate, sodium phosphate, sodium acetate, and sodium bicarbonate. These agents can be present in such an amount that the pH of a system can be maintained between 2 and 9, and preferably between 4 and 8.

There is no particular limitation on the formulation of the pharmaceutical composition of the present invention, but examples thereof include injections (an intramuscular injection, a hypodermic injection, an intradermal injection), oral formulations, and nasal formulations when a form of vaccine is used. When the pharmaceutical composition of the present invention is in a form of vaccine, a mixed cocktail vaccine containing a plurality of types of active components may be used. For example, such vaccine can contain a plurality of types of active components that is a combination of any two or more peptides of Sequence ID Nos. 1 to 12 or other active components.

The vaccine of the present invention may be inert component-containing vaccine containing a component other than the pharmaceutical composition, the component being inert itself and having an effect of further improving the effect of the pharmaceutical composition as vaccine. Examples of the inert component include an adjuvant and a toxoid. Examples of the adjuvant include sedimentary adjuvants such as aluminum hydroxide, aluminum phosphate, and potassium phosphate, and oily adjuvants such as Freund's complete adjuvant and Freund's incomplete adjuvant.

When the pharmaceutical composition of the present invention is present in a form of vaccine, it is preferable to administer the pharmaceutical composition of the present invention to the body by an injection or infusion through intradermal administration, hypodermic administration, intravenous administration, intramuscular administration, or the like, or by transdermal inhalation or inhalation through a mucous membrane of the nose, the pharynx, or the like. A dose thereof can be set to be between such an amount that a cytotoxic T cell can be significantly induced and such an amount that a significant number of non-cancer cells are not injured.

The pharmaceutical composition of the present invention is intended to be not only administered to a human body but also used outside the body. More specifically, the pharmaceutical composition of the present invention may be used to stimulate an antigen presenting cell in vitro or ex vivo and increase a CTL-inducing activity. For example, the following is description of an example of a case where the pharmaceutical composition of the present invention is used in a dendritic cell therapy for cancer. The pharmaceutical composition of the present invention can be administered to a patient requiring treatment or prevention of cancer by bringing the pharmaceutical composition into contact with an antigen presenting cell such as a dendritic cell derived from the patient in advance, and then putting the antigen presenting cell back to the body of the patient. The peptide contained in the pharmaceutical composition can be introduced into the antigen presenting cell using a lipofection method, an injection method, or the like. When a polynucleotide coding for the peptide of the present invention is used for such an application, the polynucleotide can be introduced into the antigen presenting cell using a method known in the art. The antigen presenting cell derived from a patient may be transformed in vitro, for example, with the target polynucleotide or a vector coding for the polynucleotide using a lipofection method, an electroporation method, a microinjection method, a cell fusion method, a DEAE dextran method, a calcium phosphate method, or the like.

3. Immunity-Inducing Agent

An immunity-inducing agent according to the present invention contains, as an active component, a peptide that includes eight or more consecutive amino acid residues of one or more amino acid sequences selected from the group consisting of Sequence ID Nos. 1 to 12, and that consists of eleven or less amino acids, preferably ten or less amino acids, and more preferably nine or less amino acids, in total, for example. The peptide contained in the immunity-inducing agent may also have the amino acid sequence of one of Sequence ID Nos. 1 to 12. The peptide is as defined above.

It is thought that the peptide of the present invention is presented on an antigen presenting cell and thus induces immunity. Therefore, the active component of the immunity-inducing agent of the present invention is not limited to the peptide of the present invention, and may be a component that can induce immunity directly or indirectly. For example, a polynucleotide coding for the peptide of the present invention or a vector including the polynucleotide, an antigen presenting cell that presents a complex between the peptide and an HLA molecule on its surface, or an exosome secreted by the antigen presenting cell, or combinations thereof may be used. Examples of the antigen presenting cell to be used include a macrophage and a dendritic cell, and it is preferable to use a dendritic cell, which has a high ability to induce CTLs.

The immunity-inducing agent of the present invention is intended to be not only administered to a human body but also used outside the body. More specifically, the immunity-inducing agent of the present invention may be used to stimulate an antigen presenting cell in vitro or ex vivo and increase a CTL-inducing activity. For example, the following is description of an example of a case where the immunity-inducing agent of the present invention is used in a dendritic cell therapy. The immunity-inducing agent of the present invention can be administered to a patient requiring immunity induction by bringing the immunity-inducing agent into contact with an antigen presenting cell such as a dendritic cell derived from the patient in advance, and then putting the antigen presenting cell back to the body of the patient. The peptide contained in the immunity-inducing agent can be introduced into the antigen presenting cell using transfection via a liposome (lipofection method), an injection method, or the like. When a polynucleotide coding for the peptide of the present invention is used for such an application, the polynucleotide can be introduced into the antigen presenting cell using a method known in the art. The antigen presenting cell derived from a patient may be transformed in vitro, for example, with the target polynucleotide or a vector expressing the polynucleotide using a lipofection method, an electroporation method, a microinjection method, a cell fusion method, a DEAE dextran method, a calcium phosphate method, or the like.

The "immunity induction" as used herein means that an immune reaction is induced, and a CTL-inducing activity of the antigen presenting cell as well as a cytotoxic activity of CTLs against cancer cells, for example, are thus increased. The "CTL induction" as used herein means that, in vitro or in vivo, CTLs that specifically recognize a certain antigen are induced or proliferated, or naive T cells are differentiated into effector cells that has an ability (cytotoxic activity) to kill target cells such as cancer cells, and/or the cytotoxic activity of CTLs is increased, due to the peptide of the present invention being presented on the surface of an antigen presenting cell. The CTL-inducing activity can be measured by evaluating the production of a cytokine (e.g., interferon (IFN)-γ by CTLs. For example, the CTL-inducing activity may be measured by evaluating, using a known highly sensitive immunoassay such as ELISPOT (Enzyme-Linked ImmunoSpot) or ELISA (Enzyme-Linked ImmunoSorbent Assay), an increase in the number of cytokine-producing cells that have been induced from precursor cells by an antigen presenting cell such as a peripheral blood mononuclear cell stimulated by the peptide of the present invention. The cytotoxic activity can also be measured using a known method such as a $^{51}Cr$ releasing method. When the above-mentioned activities increase significantly, for example, by 5% or more, 10% or more, or 20% or more, or preferably 50% or more, compared with control samples, immunity and CTLs can be evaluated as being induced.

4. Method for Manufacturing Antigen Presenting Cell

A method for manufacturing an antigen presenting cell according to the present invention includes a step of bringing a peptide that includes eight or more consecutive amino acid residues of one or more amino acid sequences selected from the group consisting of Sequence ID Nos. 1 to 12, and that consists of eleven or less amino acids, preferably ten or less amino acids, and more preferably nine or less amino acids, in total into contact with an antigen presenting cell in vitro, for example. The peptide used in the manufacturing method of the present invention may also have the amino acid sequence of one of Sequence ID Nos. 1 to 12. The peptide is as defined above.

It is thought that the peptide used in the manufacturing method of the present invention binds to an HLA class-I molecule on the surface of an antigen presenting cell and is presented to CTLs as an antigen peptide, and the CTL activity of the antigen presenting cell is thus induced. Therefore, a component to be brought into contact with an antigen presenting cell is not limited to the peptide of the present invention, and may be a component that can induce CTLs directly or indirectly. For example, a polynucleotide coding for the peptide or a vector including the polynucleotide, an antigen presenting cell that presents a complex between the peptide and an HLA molecule on its surface, or an exosome secreted by the antigen presenting cell, or combinations thereof may be used. Examples of the antigen presenting cell to be used include a macrophage and a dendritic cell, and it is preferable to use a dendritic cell, which has a high ability to induce CTLs.

The antigen presenting cell manufactured using the manufacturing method of the present invention is intended to be used not only as an active component of the above-mentioned pharmaceutical composition or immunity-inducing agent but also in an immunotherapy or the like. For example, the following is description of an example of a case where the manufactured antigen presenting cell is used in a dendritic cell therapy for cancer. The manufactured antigen presenting cell can be administered to a patient requiring immunity induction by bringing the manufactured antigen presenting cell into contact with an antigen presenting cell such as a dendritic cell that are derived from the patient and has a low ability to induce CTLs in advance, and then putting the manufactured antigen presenting cell back to the body of the patient. The peptide of the present invention can be introduced into the antigen presenting cell using transfection via a liposome (lipofection method), an injection method, or the like. When a polynucleotide coding for the peptide of the present invention is used for such an application, the polynucleotide can be introduced into the antigen presenting cell using a method known in the art. The antigen presenting cell derived from a patient may be transformed in vitro, for example, with the target polynucleotide or a vector coding for the polynucleotide using a lipofection method, an electroporation method, a microinjection method, a cell fusion method, a DEAE dextran method, a calcium phosphate method, or the like.

EXAMPLE 1

Hereinafter, the present invention will be described more specifically by use of examples, but the present invention is not limited to the examples.

Specifically, procedures of prediction, experiment, and evaluation in these examples were carried out based on the active learning experiment design described in WO 2006/004182, and rules were constructed by repeating the following steps as a whole.

(1) A trial of a lower-order learning algorithm, which will be described later, was carried out once. That is, a plurality of hypotheses were generated by random resampling from accumulated data, and with regard to randomly expressed candidate query points (peptides), a point that showed the largest distribution of predicted values was selected as a query point to be subjected to an experiment.

(2) The peptide at the selected query point was prepared by a synthesis and purification method, which will be described later, and the actual binding ability was measured by an experiment, which will be described later, and added to the accumulated data.

In accordance with such an active learning method, the number of repetitions of the binding experiment for peptides consisting of 9 amino acid residues, which would otherwise have to be carried out for the 500 billion ($=20^9$) or more combinations of all the candidates for HLA-binding peptides, could be reduced.

Based on the rules as described above, the amino acid sequences of Sequence ID Nos. 1 to 12 were extracted.

Synthesis and Purification of Peptide

Peptides having amino acid sequences of Sequence ID Nos. 1 to 12 were manually synthesized with the Merrifield solid-phase method using Fmoc amino acids. After deprotection, reverse phase HPLC purification was carried out using a C18 column to give a purity of 95% or higher. MALDI-TOF mass spectrometry (AB SCIEX MALDI-TOF/TOF5800) was carried out to identify the peptides and confirm their purities. The peptides were quantified with Micro BCA assay (Thermo Scientific) using BSA as a standard protein.

Experiment of Binding Peptide to HLA-A*24:02 Molecule

The ability of each of the peptides to bind to an HLA-A*24:02 molecule, which is an HLA-A*24:02 gene product, was measured using C1R-A24 cells expressing the HLA-A*24:02 molecule (cells prepared by Professor Masafumi TAKIGUCHI, Kumamoto University being supplied with permission by Assistant Professor Masaki YASUKAWA, Ehime University).

First, C1R-A24 cells were exposed to acidic conditions at a pH of 3.3 for 30 seconds, and thus an endogenous peptide that originally binds to the HLA-A*24:02 molecule, and a light chain β2m, which is associated with HLA class-I molecules in common, were dissociated and removed. After neutralization, a purified β2m was added to C1R-A24 cells, and the obtained product was added to a series of dilutions of the peptide and incubated on ice for 4 hours. Staining was carried out using a fluorescently labeled monoclonal antibody 17A12, which recognizes association (MHC-pep) of the three members, that is, a HLA-A*24:02 molecule, a peptide, and β2m, which had reassociated during the incubation.

Thereafter, the MHC-pep count per C1R-A24 cell (proportional to the intensity of fluorescence of the above-mentioned fluorescent antibody) was quantitatively measured using a fluorescence-activated cell sorter FACScan (Becton-Dickinson). A binding-dissociation constant Kd value between the HLA-A*24:02 molecule and the peptide was calculated from the average intensity of fluorescence per cell using a method that was reported in a paper (Udaka et al., Immunogenetics, 51, 816-828, 2000) by the inventors of the present invention.

Experiment of Binding Peptide to HLA-A*02:01 Molecule

The ability of each of the peptides to bind to an HLA-A*02:01 molecule, which is an HLA-A*02:01 gene product, was measured using a cell line T2 (purchased from ATCC) expressing the HLA-A*02:01 molecule.

The T2 cells and purified β2m were added to a series of serial dilutions of the peptide whose binding ability would be measured, and then incubation was carried out at 37° C. for 4 hours. The HLA-A*02:01 molecule that had increased in an expression amount in a peptide-concentration-dependent manner up to this point was stained using a fluorescently labeled monoclonal antibody BB7.2, which is specific to an association type.

Thereafter, the amount of fluorescence per cell was measured using a flow cytometer, and a dissociation constant Kd value was calculated using a method that was reported in a paper (Udaka et al., Immunogenetics, 51, 816-828, 2000) by the inventors of the present invention.

Experiment of Binding Peptide to HLA-A*02:06 Molecule

The ability of each of the peptides to bind to an HLA-A*02:06 molecule, which is an HLA-A*02:06 gene product, was measured using RA2.6 cells (cell line that had been newly produced in Kochi University) produced by introducing the cDNA of the HLA-A*02:06 gene into a mouse TAP (transporter associated with antigen processing)-deficient cell line RMAS.

First, RA2.6 cells were cultured at 26° C. overnight. After HLA-A*02:06 molecules to which the peptide did not bind accumulated on the cell surface, a series of dilutions of the peptide were added thereto, and binding was carried out at 26° C. for 60 minutes.

Thereafter, the cells were cultured at 35° C. for 4 hours. As a result, blank HLA-A*02:06 molecules to which the peptide did not bind were denatured, and thus their conformation was lost. A fluorescently labeled monoclonal antibody BB7.2, which specifically recognizes a peptide-binding HLA-A*02:06 molecule, was added thereto, incubation was carried out on ice for 20 minutes, and thus the cells were stained.

Thereafter, the amount of fluorescence per cell was measured using a flow cytometer, and a dissociation constant Kd value was calculated using a method that was reported in a paper (Udaka et al., Immunogenetics, 51, 816-828, 2000) by the inventors of the present invention.

Evaluation Results of Binding Experiments

As a result, as shown in a table below, the data from the experiment of binding the peptides of the present invention to the HLA molecules were obtained.

TABLE 2

| Amino acid sequence (Sequence ID No.) | Location in MUC1 | Data of binding experiment | | |
|---|---|---|---|---|
| | | to A*24:02 | to A*02:01 | to A*02:06 |
| FLGLSNIKF (Seq. ID No. 1) | 1086 | −7.073261692 | −5.390853526 | −4.386007431 |
| SVPVTRPAL (Seq. ID No. 2) | 100 | −7.241740934 | −3.903379214 | −5.627441171 |
| GVPGWGIAL (Seq. ID No. 3) | 1155 | −5.927200496 | −4.54796761 | −5.763029942 |
| AFREGTINV (Seq. ID No. 4) | 1106 | −5.834149762 | >−3 | >−3 |
| AASRYNLTI (Seq. ID No. 5) | 1128 | −6.148024331 | −4.811130083 | −3.824201259 |
| LQRDISEMF (Seq. ID No. 6) | 1069 | −6.646212952 | >−3 | −4.260522119 |
| HHSDTPTTL (Seq. ID No. 7) | 997 | −5.867440069 | >−3 | >−3 |
| SFFFLSFHI (Seq. ID No. 8) | 1041 | −7.065109329 | >−4 | −3.980495237 |
| TLAFREGTI (Seq. ID No. 9) | 1104 | −5.973982835 | >−3 | −3.08622966 |
| STGVSFFFL (Seq. ID No. 10) | 1037 | −5.171414811 | −5.121912366 | −5.208079724 |
| GQDVTSVPV (Seq. ID No. 11) | 95 | >−3 | −6.437064471 | −6.349002291 |
| FSAQSGAGV (Seq. ID No. 12) | 1148 | >−3 | −4.74018 | −5.661074048 |

It should be noted that the amino acid sequences of Sequence ID Nos. 1 to 12 are derived from the entire sequence (Sequence ID No. 13) (>sp|P15941|MUC1_HUMAN Mucin-1 OS=Homo sapiens GN=MUC1 PE=1 SV=3) of a predetermined MUC1 genome protein registered in GENBANK.

Peptide Immunity Induction Testing (1) Preparation of Peptide-Stimulated Dendritic Cell Day 0 to 9 (Induction of Dendritic Cell)

Of the peripheral blood monocytes obtained through pheresis from a patient (0) that had undergone a dendritic cell/CTL therapy against MUC1, a cell fraction that adhered to a culture flask was cultured in an AIM-CM culture medium (manufactured by Gibco) at 37° C. for 10 days. During the culture, 15 μl of IL-4 and 30 μl of a granulocyte monocyte colony-stimulating factor (GM-CSF) added to the culture medium on Day 0 and Day 3, and 15 μl of IL-4, 30 μl of GM-CSF, and 75 μl of a tumor necrosis factor (TFN)-α were added thereto on Day 5.

Day 10 (Peptide Stimulation and Dendritic Cell Collection)

Induced dendritic cells were collected in a new AIM-CM culture medium, and the peptide of the present invention (Sequence ID Nos. 1 to 12) was added thereto to a concentration of 20 μg/ml. Thereafter, the culture medium containing the dendritic cells was cultured at 37° C. for 2 hours. The following peptides were used as positive controls and negative controls.

Positive control for HLA-A*24:02 (EBV LMP2, 419-427: TYGPVFMCL (Sequence ID No. 14))

Negative control for HLA-A*24:02 (HIV env gp160, 584-592: RYLRDQQLL (Sequence ID No. 15))

Positive control for HLA-A*02:01 (Flu A MP, 58-66: GILGFVFTL (Sequence ID No. 16))

Negative control for HLA-A*02:01 (HIV gap p17, 77-85: SLYNTVATL (Sequence ID No. 17))

Positive control for HLA-A*02:06 (EBV LMP2 453-461: LTAGFLIFL (Sequence ID No. 18))

Negative control for HLA-A*02:06 (HIV gap p24 341-349: ATLEEMMTA (Sequence ID No. 19))

The dendritic cells were collected and washed three or more times using a sufficient amount of an AIM-CM culture medium, and then the number of cells was counted.

(2) Preparation of CD8T Cells

Day 0 to 9

Of the peripheral blood monocytes obtained through pheresis from a patient that had undergone treatment using the above-mentioned vaccine twice or more, a floating cell fraction (containing lymphocytes) that did not adhere to a culture flask was cultured in an AIM-CM culture medium (manufactured by Gibco) at 37° C. for 10 days. During the culture, 40 μl of IL-2 was added to the culture medium on Day 4 and Day 6.

Day 10

CD8T cells were isolated from the culture medium using a CD8 negative selection kit (manufactured by Miltenyi), and the number of cells was counted.

(3) Coculture

The dendritic cells and CD8T cells obtained in the above (1) and (2) were cocultured in an AIM-CM culture medium at 37° C. in the following conditions.

CD8T cell: 5×10$^5$ cells/well

Dendritic cell: 2×10$^5$ cells/well

Day 12 or 13

To the above-mentioned culture medium, 0.4 ml/well of an AIM-CM culture medium containing 20 U/ml of IL-2 was added.

(5) ELISA Assay

Day 17

Figure 2:
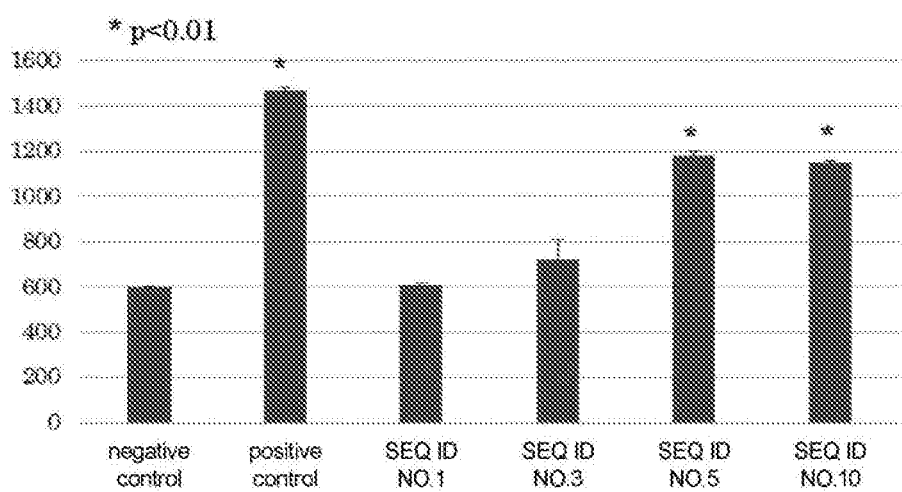
FIG. 2 shows results (the number of IFN-γ producing cells) of ELISA assay when samples from a patient (HLA type: 11:01/24:02) that has undergone a dendritic cell/CTL therapy against MUC1 are stimulated using peptides of Sequence ID Nos. 1, 3, 5, and 10.
Figure 3:
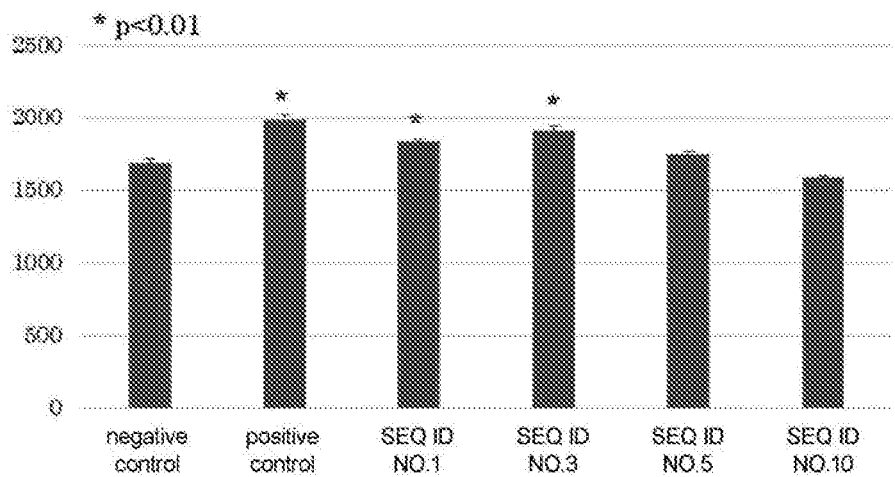
FIG. 3 shows results (the number of IFN-γ producing cells) of ELISA assay when samples from a patient (HLA type: 02:06/24:02) that has undergone a dendritic cell/CTL therapy against MUC1 are stimulated using peptides of Sequence ID Nos. 1, 3, 5, and 10.
Figure 4:
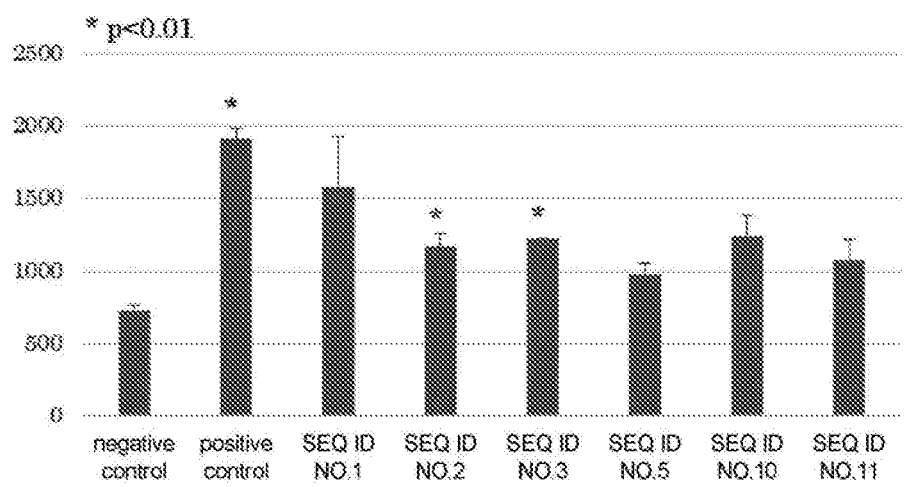
FIG. 4 shows results (the number of IFN-y producing cells) of ELISA assay when samples from a patient (HLA type: 02:01/02:06) that has undergone a dendritic cell/CTL therapy against MUC1 are stimulated using peptides of Sequence ID Nos. 1, 2, 3, 5, 10, and 11.

The culture supernatant of the coculture of the T cells and the dendritic cells pulsed with the above-mentioned peptides on Day 7 was diluted to four steps, that is, ×1, ×5, ×25, and ×125, and the dilution step within a measurement limit was identified using Human IFN-γ ELISA MAX Deluxe Set (manufactured by BioLegend). Thereafter, at the identified dilution step, each sample was measured three times. FIGS. 1 to 4 respectively show typical results of ELISA assay from a patient with an HLA type of 24:02/33:03, a patient with an HLA type of 11:01/24:02, a patient with an HLA type of 02:06/24:02, and a patient having an HLA type of 02:01/02:06.

The present invention has been described based on the examples. The examples are merely exemplary, and a person skilled in the art would understand that various modified examples are possible, and such modified examples are also within a scope of the present invention.

The invention claimed is:

1. A method of inducing immunity comprising:

administrating a peptide to a subject, wherein the peptide consists of a variant of the amino acid sequence of SEQ ID NO: 3, wherein in the variant, the amino acid at 2-position of the sequence in SEQ ID NO: 3 is substituted with tyrosine, phenylalanine, tryptophan, valine or glutamine, and the C-terminal amino acid of the sequence in SEQ ID NO: 3 is substituted with phenylalanine, isoleucine, tryptophan or methionine, and the peptide can bind to one or more types of HLA-A molecules.

2. The method according to claim 1, wherein the peptide induces a cytotoxic T cell.

3. The method according to claim 1, wherein the method is a method of inducing a cytotoxic T cell.

4. The method according to claim 1, further comprising contacting the peptide and antigen-presenting cells in vitro, wherein the obtained antigen-presenting cells are administered to the subject as the peptide in the administrating step.

* * * * *

SEQUENCE LISTING

```
<160> NUMBER OF SEQ ID NOS: 19

<210> SEQ ID NO 1
<211> LENGTH: 9
<212> TYPE: PRT
<213> ORGANISM: Homo sapiens

<400> SEQUENCE: 1

Phe Leu Gly Leu Ser Asn Ile Lys Phe
1               5

<210> SEQ ID NO 2
<211> LENGTH: 9
<212> TYPE: PRT
<213> ORGANISM: Homo sapiens

<400> SEQUENCE: 2

Ser Val Pro Val Thr Arg Pro Ala Leu
1               5
```

```
<210> SEQ ID NO 3
<211> LENGTH: 9
<212> TYPE: PRT
<213> ORGANISM: Homo sapiens

<400> SEQUENCE: 3

Gly Val Pro Gly Trp Gly Ile Ala Leu
1               5

<210> SEQ ID NO 4
<211> LENGTH: 9
<212> TYPE: PRT
<213> ORGANISM: Homo sapiens

<400> SEQUENCE: 4

Ala Phe Arg Glu Gly Thr Ile Asn Val
1               5

<210> SEQ ID NO 5
<211> LENGTH: 9
<212> TYPE: PRT
<213> ORGANISM: Homo sapiens

<400> SEQUENCE: 5

Ala Ala Ser Arg Tyr Asn Leu Thr Ile
1               5

<210> SEQ ID NO 6
<211> LENGTH: 9
<212> TYPE: PRT
<213> ORGANISM: Homo sapiens

<400> SEQUENCE: 6

Leu Gln Arg Asp Ile Ser Glu Met Phe
1               5

<210> SEQ ID NO 7
<211> LENGTH: 9
<212> TYPE: PRT
<213> ORGANISM: Homo sapiens

<400> SEQUENCE: 7

His His Ser Asp Thr Pro Thr Thr Leu
1               5

<210> SEQ ID NO 8
<211> LENGTH: 9
<212> TYPE: PRT
<213> ORGANISM: Homo sapiens

<400> SEQUENCE: 8

Ser Phe Phe Phe Leu Ser Phe His Ile
1               5

<210> SEQ ID NO 9
<211> LENGTH: 9
<212> TYPE: PRT
<213> ORGANISM: Homo sapiens

<400> SEQUENCE: 9

Thr Leu Ala Phe Arg Glu Gly Thr Ile
1               5

<210> SEQ ID NO 10
```

```
<211> LENGTH: 9
<212> TYPE: PRT
<213> ORGANISM: Homo sapiens

<400> SEQUENCE: 10

Ser Thr Gly Val Ser Phe Phe Phe Leu
1               5

<210> SEQ ID NO 11
<211> LENGTH: 9
<212> TYPE: PRT
<213> ORGANISM: Homo sapiens

<400> SEQUENCE: 11

Gly Gln Asp Val Thr Ser Val Pro Val
1               5

<210> SEQ ID NO 12
<211> LENGTH: 9
<212> TYPE: PRT
<213> ORGANISM: Homo sapiens

<400> SEQUENCE: 12

Phe Ser Ala Gln Ser Gly Ala Gly Val
1               5

<210> SEQ ID NO 13
<211> LENGTH: 1255
<212> TYPE: PRT
<213> ORGANISM: Homo sapiens

<400> SEQUENCE: 13

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
                20                  25                  30

Gly Glu Lys Glu Thr Ser Ala Thr Gln Arg Ser Ser Val Pro Ser Ser
            35                  40                  45

Thr Glu Lys Asn Ala Val Ser Met Thr Ser Ser Val Leu Ser Ser His
        50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
                100                 105                 110

Pro Pro Ala His Asp Val Thr Ser Ala Pro Asp Asn Lys Pro Ala Pro
            115                 120                 125

Gly Ser Thr Ala Pro Pro Ala His Gly Val Thr Ser Ala Pro Asp Thr
        130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
                180                 185                 190

Pro Pro Ala His Gly Val Thr Ser Ala Pro Asp Thr Arg Pro Ala Pro
            195                 200                 205

Gly Ser Thr Ala Pro Pro Ala His Gly Val Thr Ser Ala Pro Asp Thr
```

```
                210                 215                 220
Arg Pro Ala Pro Gly Ser Thr Ala Pro Pro Ala His Gly Val Thr Ser
225                 230                 235                 240

Ala Pro Asp Thr Arg Pro Ala Pro Gly Ser Thr Ala Pro Pro Ala His
                245                 250                 255

Gly Val Thr Ser Ala Pro Asp Thr Arg Pro Ala Pro Gly Ser Thr Ala
                260                 265                 270

Pro Pro Ala His Gly Val Thr Ser Ala Pro Asp Thr Arg Pro Ala Pro
                275                 280                 285

Gly Ser Thr Ala Pro Pro Ala His Gly Val Thr Ser Ala Pro Asp Thr
                290                 295                 300

Arg Pro Ala Pro Gly Ser Thr Ala Pro Pro Ala His Gly Val Thr Ser
305                 310                 315                 320

Ala Pro Asp Thr Arg Pro Ala Pro Gly Ser Thr Ala Pro Pro Ala His
                325                 330                 335

Gly Val Thr Ser Ala Pro Asp Thr Arg Pro Ala Pro Gly Ser Thr Ala
                340                 345                 350

Pro Pro Ala His Gly Val Thr Ser Ala Pro Asp Thr Arg Pro Ala Pro
                355                 360                 365

Gly Ser Thr Ala Pro Pro Ala His Gly Val Thr Ser Ala Pro Asp Thr
                370                 375                 380

Arg Pro Ala Pro Gly Ser Thr Ala Pro Pro Ala His Gly Val Thr Ser
385                 390                 395                 400

Ala Pro Asp Thr Arg Pro Ala Pro Gly Ser Thr Ala Pro Pro Ala His
                405                 410                 415

Gly Val Thr Ser Ala Pro Asp Thr Arg Pro Ala Pro Gly Ser Thr Ala
                420                 425                 430

Pro Pro Ala His Gly Val Thr Ser Ala Pro Asp Thr Arg Pro Ala Pro
                435                 440                 445

Gly Ser Thr Ala Pro Pro Ala His Gly Val Thr Ser Ala Pro Asp Thr
                450                 455                 460

Arg Pro Ala Pro Gly Ser Thr Ala Pro Pro Ala His Gly Val Thr Ser
465                 470                 475                 480

Ala Pro Asp Thr Arg Pro Ala Pro Gly Ser Thr Ala Pro Pro Ala His
                485                 490                 495

Gly Val Thr Ser Ala Pro Asp Thr Arg Pro Ala Pro Gly Ser Thr Ala
                500                 505                 510

Pro Pro Ala His Gly Val Thr Ser Ala Pro Asp Thr Arg Pro Ala Pro
                515                 520                 525

Gly Ser Thr Ala Pro Pro Ala His Gly Val Thr Ser Ala Pro Asp Thr
                530                 535                 540

Arg Pro Ala Pro Gly Ser Thr Ala Pro Pro Ala His Gly Val Thr Ser
545                 550                 555                 560

Ala Pro Asp Thr Arg Pro Ala Pro Gly Ser Thr Ala Pro Pro Ala His
                565                 570                 575

Gly Val Thr Ser Ala Pro Asp Thr Arg Pro Ala Pro Gly Ser Thr Ala
                580                 585                 590

Pro Pro Ala His Gly Val Thr Ser Ala Pro Asp Thr Arg Pro Ala Pro
                595                 600                 605

Gly Ser Thr Ala Pro Pro Ala His Gly Val Thr Ser Ala Pro Asp Thr
                610                 615                 620

Arg Pro Ala Pro Gly Ser Thr Ala Pro Pro Ala His Gly Val Thr Ser
625                 630                 635                 640
```

Ala Pro Asp Thr Arg Pro Ala Pro Gly Ser Thr Ala Pro Ala His
                    645                 650                 655

Gly Val Thr Ser Ala Pro Asp Thr Arg Pro Ala Pro Gly Ser Thr Ala
                660                 665                 670

Pro Pro Ala His Gly Val Thr Ser Ala Pro Asp Thr Arg Pro Ala Pro
            675                 680                 685

Gly Ser Thr Ala Pro Pro Ala His Gly Val Thr Ser Ala Pro Asp Thr
        690                 695                 700

Arg Pro Ala Pro Gly Ser Thr Ala Pro Pro Ala His Gly Val Thr Ser
705                 710                 715                 720

Ala Pro Asp Thr Arg Pro Ala Pro Gly Ser Thr Ala Pro Pro Ala His
                725                 730                 735

Gly Val Thr Ser Ala Pro Asp Thr Arg Pro Ala Pro Gly Ser Thr Ala
                740                 745                 750

Pro Pro Ala His Gly Val Thr Ser Ala Pro Asp Thr Arg Pro Ala Pro
            755                 760                 765

Gly Ser Thr Ala Pro Pro Ala His Gly Val Thr Ser Ala Pro Asp Thr
        770                 775                 780

Arg Pro Ala Pro Gly Ser Thr Ala Pro Pro Ala His Gly Val Thr Ser
785                 790                 795                 800

Ala Pro Asp Thr Arg Pro Ala Pro Gly Ser Thr Ala Pro Pro Ala His
                805                 810                 815

Gly Val Thr Ser Ala Pro Asp Thr Arg Pro Ala Pro Gly Ser Thr Ala
                820                 825                 830

Pro Pro Ala His Gly Val Thr Ser Ala Pro Asp Thr Arg Pro Ala Pro
            835                 840                 845

Gly Ser Thr Ala Pro Pro Ala His Gly Val Thr Ser Ala Pro Asp Thr
        850                 855                 860

Arg Pro Ala Pro Gly Ser Thr Ala Pro Pro Ala His Gly Val Thr Ser
865                 870                 875                 880

Ala Pro Asp Thr Arg Pro Ala Pro Gly Ser Thr Ala Pro Pro Ala His
                885                 890                 895

Gly Val Thr Ser Ala Pro Asp Thr Arg Pro Ala Pro Gly Ser Thr Ala
                900                 905                 910

Pro Pro Ala His Gly Val Thr Ser Ala Pro Asp Thr Arg Pro Ala Pro
            915                 920                 925

Gly Ser Thr Ala Pro Pro Ala His Gly Val Thr Ser Ala Pro Asp Asn
        930                 935                 940

Arg Pro Ala Leu Gly Ser Thr Ala Pro Pro Val His Asn Val Thr Ser
945                 950                 955                 960

Ala Ser Gly Ser Ala Ser Gly Ser Ala Ser Thr Leu Val His Asn Gly
                965                 970                 975

Thr Ser Ala Arg Ala Thr Thr Thr Pro Ala Ser Lys Ser Thr Pro Phe
            980                 985                 990

Ser Ile Pro Ser His His Ser Asp Thr Pro Thr Thr Leu Ala Ser His
            995                 1000                1005

Ser Thr Lys Thr Asp Ala Ser Ser Thr His His Ser Ser Val Pro
        1010                1015                1020

Pro Leu Thr Ser Ser Asn His Ser Thr Ser Pro Gln Leu Ser Thr
        1025                1030                1035

Gly Val Ser Phe Phe Phe Leu Ser Phe His Ile Ser Asn Leu Gln
        1040                1045                1050

```
Phe Asn Ser Ser Leu Glu Asp Pro Ser Thr Asp Tyr Tyr Gln Glu
    1055                1060                1065

Leu Gln Arg Asp Ile Ser Glu Met Phe Leu Gln Ile Tyr Lys Gln
    1070                1075                1080

Gly Gly Phe Leu Gly Leu Ser Asn Ile Lys Phe Arg Pro Gly Ser
    1085                1090                1095

Val Val Val Gln Leu Thr Leu Ala Phe Arg Glu Gly Thr Ile Asn
    1100                1105                1110

Val His Asp Val Glu Thr Gln Phe Asn Gln Tyr Lys Thr Glu Ala
    1115                1120                1125

Ala Ser Arg Tyr Asn Leu Thr Ile Ser Asp Val Ser Val Ser Asp
    1130                1135                1140

Val Pro Phe Pro Phe Ser Ala Gln Ser Gly Ala Gly Val Pro Gly
    1145                1150                1155

Trp Gly Ile Ala Leu Leu Val Leu Val Cys Val Leu Val Ala Leu
    1160                1165                1170

Ala Ile Val Tyr Leu Ile Ala Leu Ala Val Cys Gln Cys Arg Arg
    1175                1180                1185

Lys Asn Tyr Gly Gln Leu Asp Ile Phe Pro Ala Arg Asp Thr Tyr
    1190                1195                1200

His Pro Met Ser Glu Tyr Pro Thr Tyr His Thr His Gly Arg Tyr
    1205                1210                1215

Val Pro Pro Ser Ser Thr Asp Arg Ser Pro Tyr Glu Lys Val Ser
    1220                1225                1230

Ala Gly Asn Gly Gly Ser Ser Leu Ser Tyr Thr Asn Pro Ala Val
    1235                1240                1245

Ala Ala Thr Ser Ala Asn Leu
    1250                1255

<210> SEQ ID NO 14
<211> LENGTH: 9
<212> TYPE: PRT
<213> ORGANISM: Homo sapiens

<400> SEQUENCE: 14

Thr Tyr Gly Pro Val Phe Met Cys Leu
1               5

<210> SEQ ID NO 15
<211> LENGTH: 9
<212> TYPE: PRT
<213> ORGANISM: Homo sapiens

<400> SEQUENCE: 15

Arg Tyr Leu Arg Asp Gln Gln Leu Leu
1               5

<210> SEQ ID NO 16
<211> LENGTH: 9
<212> TYPE: PRT
<213> ORGANISM: Homo sapiens

<400> SEQUENCE: 16

Gly Ile Leu Gly Phe Val Phe Thr Leu
1               5

<210> SEQ ID NO 17
<211> LENGTH: 9
<212> TYPE: PRT
```

```
<213> ORGANISM: Homo sapiens

<400> SEQUENCE: 17

Ser Leu Tyr Asn Thr Val Ala Thr Leu
1               5

<210> SEQ ID NO 18
<211> LENGTH: 9
<212> TYPE: PRT
<213> ORGANISM: Homo sapiens

<400> SEQUENCE: 18

Leu Thr Ala Gly Phe Leu Ile Phe Leu
1               5

<210> SEQ ID NO 19
<211> LENGTH: 9
<212> TYPE: PRT
<213> ORGANISM: Homo sapiens

<400> SEQUENCE: 19

Ala Thr Leu Glu Glu Met Met Thr Ala
1               5
```